(12) United States Patent
Kumari et al.

(10) Patent No.: US 6,693,211 B2
(45) Date of Patent: Feb. 17, 2004

(54) CHEMICAL PROCESS

(75) Inventors: Durga Kumari, North Brunswick, NJ (US); Mahendra R. Patel, East Brunswick, NJ (US)

(73) Assignee: Geneva Pharmaceuticals, Inc., Broomfield, CO (US)

( * ) Notice: Subject to any disclaimer, the term of this patent is extended or adjusted under 35 U.S.C. 154(b) by 0 days.

(21) Appl. No.: 10/424,632

(22) Filed: Apr. 28, 2003

(65) Prior Publication Data

US 2003/0216566 A1 Nov. 20, 2003

Related U.S. Application Data

(60) Provisional application No. 60/380,661, filed on May 15, 2002.

(51) Int. Cl.$^7$ ............................................. C07F 15/02
(52) U.S. Cl. .................... 556/146; 556/147; 424/647; 514/53
(58) Field of Search .............................. 556/146, 147; 514/53; 424/647

(56) References Cited

U.S. PATENT DOCUMENTS

| | | | | |
|---|---|---|---|---|
| 3,873,588 A | * | 3/1975 | Osawa et al. ................ | 556/147 |
| 4,786,518 A | | 11/1988 | Nakel ......................... | 426/531 |
| 4,975,290 A | * | 12/1990 | Artz et al. ................... | 426/74 |
| 5,284,832 A | | 2/1994 | Ferrari ........................ | 514/21 |
| 6,537,820 B2 | * | 3/2003 | Beck et al. .................. | 436/84 |
| 2002/0076821 A1 | | 6/2002 | Beck .......................... | 436/74 |

FOREIGN PATENT DOCUMENTS

| | | |
|---|---|---|
| DE | 3844065 | 7/1990 |
| EP | 0563753 A | 10/1993 |
| GB | 879441 | 10/1961 |
| WO | WO 02/056826 A2 | 7/2002 |

OTHER PUBLICATIONS

Chem Abstract for JP 33005647, Takeda, Jul. 28, 1958; Accession No. 53:19317e–f CA.

Studies on Iron Complexes I, Yakugaku Zasshi 78, 951–957 (1958); Tanabe and Okada, Full English text and CA abstract.

Studies on Iron Complexes II, Takeda Kenkyusho Nempo 21, 1–10 (1962), Full English text and CA abstract.

Tanabe and Okada, Tanabe and Okada, Studies on Iron Complexes III, Takeda Kenkyusho Nempo 21, 11–19 (1962); (full text not attached, CA abstract only).

Tanabe and Okada, Studies on Iron Complexes IV, Takeda Kenkyusho Nempo 21, 20–25 (1962), Full English text and CA abstract.

Faich and Strobos, American Journal of Kidney Disease Online, Mar. 1999, Vol 33, No 3, 9 pages.

Derwent 97–181010/17, BOEF Sep. 14, 1995, abstract of DE 19535571–A1 (also text of DE patent in German language).

* cited by examiner

*Primary Examiner*—James H Reamer
(74) *Attorney, Agent, or Firm*—Hesna J. Pfeiffer

(57) ABSTRACT

This invention provides a process for preparing sodium ferric gluconate complex in sucrose using the following steps:

a) combining a ferric salt solution with a weak alkali chosen from the group consisting of alkaline earth metal and ammonium salts, such as sodium carbonate, sodium bicarbonate, lithium carbonate, potassium carbonate, potassium bicarbonate, ammonium carbonate, ammonium bicarbonate and mixtures thereof, to form the ferric oxyhydroxide;

b) combining ferric oxyhydroxide and sodium gluconate in solution to yield the sodium ferric gluconate complex;

c) isolating the sodium ferric gluconate complex; and d) combining the sodium ferric gluconate with sucrose in solution to yield the desired sodium ferric gluconate complex in sucrose.

3 Claims, No Drawings

CHEMICAL PROCESS

This application claims the benefit of Provisional Application Ser. No. 60/380,661 filed May 15, 2002.

FIELD OF INVENTION

This present invention relates to the process for preparing sodium ferric gluconate complex in sucrose.

1. Background of the Invention

Sodium ferric gluconate complex in sucrose has been known for about 40 years. It has been utilized primarily as an injectable agent for treating iron deficiencies in animals and human patients, having several advantages over other iron preparations including low toxicity, low incidence of adverse reactions, and satisfactory rate of iron absorption.

The material has been studied, see "Studies on Iron Complexes I", Yakugaku Zasshi Vol. 78, pp. 951–957 (1958); Tanabe and Okada, "Studies on Iron Complexes II", Takeda Kenkyusho Nempo, Vol. 21, pp. 1–10 (1962); Tanabe and Okada, "Studies on Iron Complexes III", Takeda Kenkyusho Nempo, Vol. 21, pp. 11–19 (1962); and Tanabe and Okada, "Studies on Iron Complexes IV", Takeda Kenkyusho Nempo, Vol. 21, pp. 20–25 (1962). Generally, the published methodology utilizes the reaction of iron hydroxide as the starting material.

2. The Problem in the Art

Literature methods of preparing sodium ferric gluconate complex in sucrose are not satisfactory, due to low yields and high cost of preparation.

BRIEF DESCRIPTION OF THE INVENTION

This invention provides a process for preparing sodium ferric gluconate complex in sucrose using the following steps:

a) combining a ferric salt solution with a weak alkali chosen from the group consisting of alkaline earth metal and ammonium salts, such as sodium carbonate, sodium bicarbonate, lithium carbonate, potassium carbonate, potassium bicarbonate, ammonium carbonate, ammonium bicarbonate and mixtures thereof, to form the ferric oxyhydroxide;

b) combining ferric oxyhydroxide and sodium gluconate in solution to yield the sodium ferric gluconate complex;

c) isolating the sodium ferric gluconate complex; and d) combining the sodium ferric gluconate with sucrose in solution to yield the desired sodium ferric gluconate complex in sucrose.

One key step in the process of this invention is the preparation of the ferric oxyhydroxide.

The ferric oxyhydroxide is prepared by neutralization of an aqueous solution of an iron (III) chloride salt with weak alkali at room temperature. This is in the form of colloidal gel, as the solid settles down and clear liquid remains at the top.

Although we do not wish to be bound by theory, the following is proposed as the scheme of formation of ferric oxyhydroxide.

$FeCl_3$ (solid)+$H_2O \rightarrow Fe^{3+}$+$3Cl^-$(in solution)

$Fe^{3+}$+$H_2O \rightleftharpoons Fe(OH)_2^+$+$H^+$(weak acidic solution)

$Fe(OH)_{2+}$+$H_2O \rightleftharpoons Fe(OH)_2^+$+$H^+$ $Fe^{3+}$+$CO_3^{-2}$ (from sodium carbonate)+$H_2O \rightarrow Fe(OH)^{+2}$+ $HCO_3^{-1}$ (in solution)

$Cl^{-1}$ (from ferric chloride)+$Na^{+1}$(from sodium carbonate or sodium bicarbonate)$\rightarrow$NaCl (in solution)

$Cl^{-1}$ (from ferric chloride)+$Li^{+1}$(from lithium carbonate) $\rightarrow$LiCl (in solution)

$Cl^{-1}$ (from ferric chloride)+$K^{+1}$(from potassium carbonate or potassium bicarbonate)$\rightarrow$KCl (in solution)

$Cl^{-1}$ (from ferric chloride)+$NH_4^{+1}$(from ammonium carbonate or ammonium bicarbonate)$\rightarrow NH_4Cl$ (in solution)

$Fe(OH)^{+2}$+$HCO_3^{-1}$+$H_2O \rightarrow Fe(OH)_2^{+1}$+$CO_2 \uparrow$(in solution)

(poly)$Fe(OH)_2^{+1}$+$CO_3^{-2}$+$H_2O \rightarrow$(poly)FeOOH (colloidal gel)+$CO_2 \uparrow$ The byproducts of this weak base neutralization of weak acidic solution of ferric chloride are chloride salt and carbon dioxide.

When attempts were made to use either ammonium hydroxide or sodium hydroxide to neutralize the ferric chloride solution, the reactions failed to form sodium ferric gluconate complex with sodium gluconate.

DETAILED DESCRIPTION OF THE INVENTION

The present invention relates to a method of making sodium ferric gluconate complex in sucrose, comprising the steps of:

a) combining an aqueous solution of ferric chloride with solid or aqueous weak alkali to a neutral pH;

b) removing chloride salts from colloidal ferric oxyhydroxide in solution;

c) adding sodium gluconate (solid) to the aqueous colloidal solution of ferric oxyhydroxide and heating to about 70–80° C. for about 2 to 3 hours or until all ferric oxyhydroxide dissolves, and produces a dark brown color;

d) drying the sodium ferric gluconate complex, e.g., using freeze-drying; and e) adding sucrose solution (about 20%) into the sodium ferric gluconate complex.

The starting materials for the reaction of this invention are:

Sucrose (α-D-glucopyranoside, β-D-fructofuranosyl-) is a disaccharide of formula $C_{12}H_{22}O_{11}$ (molecular weight=342.30). CAS=57-50-1. Sucrose is a sugar obtained from saccharum fininarum Linne (family gramineae), Beta vulgaris Linne (family Chenopodiaceae), and other sources.

Sodium gluconate (D-gluconic acid, monosodium salt) is of formula $C_6H_{11}NaO_7$ (molecular weight=218.14).

The iron salt used as the starting material can be any which is available. We choose ferric salts to minimize expense. The ferric salt is preferably ferric chloride hexahydrate, although other ferric chloride forms or ferric salts can be used.

In the first step of the process of the invention, ferric chloride hexahydrate is dissolved in water and adding quantitatively the weak base such as carbonate salt solution to neutral pH to precipitate ferric oxyhydroxide. The colloidal ferric oxyhydroxide is formed along with chloride salts in solution.

The weak base can be chosen from the group consisting of alkaline earth metal and ammonium salts, such as sodium carbonate, sodium bicarbonate, lithium carbonate, potassium carbonate, potassium bicarbonate, ammonium carbonate, ammonium bicarbonate and mixtures thereof. It can be employed either as a solid added to the aqueous solution of the ferric chloride or in aqueous solution. It is used in quantitative amounts to the ferric chloride.

In the next step, chloride salt is removed by several times washing with deionized water, which is pipetted out or siphoned off.

The washed ferric oxyhydroxide is then suspended in water and solid sodium gluconate is added. The ratio of ferric salt to sodium gluconate is 2:1, although the ratio can be as low as 1.5 to 1, or as high as 4:1. The solution is then heated to about 70–80° C. for about 2 to 3 hours or until all ferric oxyhydroxide dissolves. The product has a dark brown color. The critical end point of this step is the dark brown color and the complete solubility of the product. When the reaction is unsuccessful, the product is a reddish or light brown; the reaction mixture has visible solids.

Once the reaction is complete, the product is dried, e.g., by freeze-drying. The material is identified by infrared spectroscopic analysis. This material is then used in the next step.

In the next step, the sodium ferric gluconate complex is mixed with 20% of aqueous sucrose at a temperature of between 80° C. and 100° C., then cooled. This product in solution is useful as the injectable drug.

The above reactions are preferably performed in a dark place or in subdued light, although this is not critical to the success of the reactions.

The following examples illustrate the invention.

EXAMPLE 1

Preparation of Sodium Ferric Gluconate Complex in Sucrose

To a solution of ferric chloride hexahydrate (6.9 g) in water (100 mL) is added gradually in about 10 minutes, sodium carbonate solution (4.09 g in 150 mL water) with continuous stirring. The colloidal ferric oxyhydroxide formed is washed several times with water (5×100 mL) to remove chloride salt (also check with silver nitrate solution). Then ferric oxyhydroxide is suspended in 250 mL of water and added 2.8 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The sodium ferric gluconate complex formed is freeze-dried. The yield of product is about 5.1 g. The material passes infrared spectroscopic analysis.

62.5 mg of iron containing sodium ferric gluconate complex (on anhydrous basis) is dissolved in 5 mL of about 20% aqueous sucrose solution, and heated for about 30 minutes at 80° C. The material passes gel permeation chromatographic analysis.

EXAMPLE 2

Preparation of Sodium Ferric Gluconate Complex in Sucrose

To a solution of ferric chloride hexahydrate (10.5 g) in water (200 mL) is added gradually sodium carbonate (6.2 g solid) with continuous stirring. The colloidal ferric oxyhydroxide formed is washed several times with water (5×150 mL) to remove the chloride salt (also check with silver nitrate solution). Then ferric oxyhydroxide is suspended in 350 mL of water and added 4.2 g of sodium gluconate at about 25° C. The mixture is stirred for about 5 minutes. Then the reaction mixture is heated to about 70–80° C. for about 2 hours or until a dark brown color is formed. The ratio of ferric oxyhydroxide to sodium gluconate in this reaction is 2:1. The sodium ferric gluconate complex formed is freeze-dried. The yield of product is about 8.0 g. The material passes infrared spectroscopic analysis.

62.5 mg of Iron containing sodium ferric gluconate complex (on anhydrous basis) is dissolved in 5 mL of about 20% aqueous sucrose solution and heated for about 30 minutes at 80° C.

EXAMPLE 3

Preparation of Sodium Ferric Gluconate Complex in Sucrose

To a solution of ferric chloride hexahydrate (9.1 g) in water (200 mL) is added gradually aqueous sodium carbonate solution (5.4 g in 150 mL of deionized water) with continuous stirring. The colloidal ferric oxyhydroxide forms and is washed several times with water (5×125 mL) to remove the chloride salt (also check with silver nitrate solution). Then ferric oxyhydroxide is suspended in 300 mL of water and 3.7 g of sodium gluconate added at about 25° C.; The mixture is stirred for about 5 minutes. Then the reaction mixture is heated to about 70–80° C. for about 2 hours until a dark brown solution forms. The ratio of ferric oxyhydroxide to sodium gluconate in this reaction is 2:1. The sodium ferric gluconate complex formed is concentrated in oven at 60° C. to form a one fourth volume and then cooled the solution to room temperature. Adding double the volume of reagent alcohol precipitates the sodium ferric gluconate complex. The precipitate is centrifuged. Supernatant is discarded and the bottom solid is washed with few mL of reagent alcohol. The bottom solids are dissolved in deionized water and freeze-dried. The yield of product is about 6.0 g. The material passes infrared spectroscopic analysis.

62.5 mg of iron containing sodium ferric gluconate complex (on anhydrous basis) is dissolved in 5 mL of 20% aqueous sucrose solution and heated for about 30 minutes at 80° C.

EXAMPLE 4

Preparation of Sodium Ferric Gluconate Complex

To a solution of ferric chloride hexahydrate (6.4 g) in water (100 mL) is added gradually solid sodium carbonate (3.8 g) with continuous stirring. The colloidal ferric oxyhydroxide formed, washed several times with water (5×100 mL) to remove the chloride salt (also check with silver nitrate solution). Then ferric oxyhydroxide is suspended in about 250 mL of deionized water. Added 1.7 g of sodium gluconate at about 25+ C. The mixture is stirred for about 5 minutes. Then the reaction mixture is heated to about 70–80° C. for about 2 hours until a dark brown solution forms. The ratio of ferric oxyhydroxide to sodium gluconate in this reaction is 3:1. The sodium ferric gluconate complex formed is freeze-dried. The yield of product is about 3.8 g. The material passes infrared spectroscopic analysis.

EXAMPLE 5

Preparation of Sodium Ferric Gluconate Complex

To a solution of ferric chloride hexahydrate (4.9 g) in water (100 mL) is added gradually in about 10 minutes, sodium carbonate solution (2.9 g in 150 mL water) with continuous stirring. The colloidal ferric oxyhydroxide formed is washed several times with water (6×75 mL) to remove chloride salt (also check with silver nitrate solution).

Then ferric oxyhydroxide is suspended in 250 mL of water and added 3.9 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 1:1. The sodium ferric gluconate complex formed is freeze-dried. The yield of product is about 5.5 g. The material passes infrared spectroscopic analysis.

EXAMPLE 6

Preparation of Sodium Ferric Gluconate Complex

To a solution of ferric chloride hexahydrate (3.8 g) in water (100 mL) is added gradually in about 10 minutes, sodium bicarbonate solution (3.6 g in 150 mL water) with continuous stirring. The colloidal ferric oxyhydroxide formed is washed several times with water (6×75 mL) to remove chloride salt (also check with silver nitrate solution). Then ferric oxyhydroxide is suspended in 250 mL of water and added 1.52 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 7

Preparation of Sodium Ferric Gluconate Complex

To a solution of ferric chloride hexahydrate (3.7 g) in water (100 mL) is added gradually in about 10 minutes, ammonium carbonate solution (3.9 g in 150 mL water) with continuous stirring. The colloidal ferric oxyhydroxide formed is washed several times with water (5×75 mL) to remove chloride salt (also check with silver nitrate solution). Then ferric oxyhydroxide is suspended in 250 mL of water and added 1.5 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 8

Preparation of Sodium Ferric Gluconate Complex

To a solution of ferric chloride hexahydrate (4.4 g) in water (100 mL) is added gradually in about 10 minutes, lithium carbonate solution (1.85 g in 150 mL water) with continuous stirring. The colloidal ferric oxyhydroxide formed is washed several times with water (5×75 mL) to remove chloride salt (also check with silver nitrate solution). Then ferric oxyhydroxide is suspended in 250 mL of water and added 1.8 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 9

Preparation of Sodium Ferric Gluconate Complex

To a solution of ferric chloride hexahydrate (3.9 g) in water (100 mL) is added gradually in about 10 minutes, potassium carbonate solution (3.6 g in 150 mL water) with continuous stirring. The colloidal ferric oxyhydroxide formed is washed several times with water (5×75 mL) to remove chloride salt (also check with silver nitrate solution). Then ferric oxyhydroxide is suspended in 250 mL of water and added 1.6 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 10

Preparation of Sodium Ferric Gluconate Complex

To a solution of ferric chloride hexahydrate (4.4 g) in water (100 mL) is added gradually in about 10 minutes, potassium bicarbonate solution (5.0 g in 150 mL water) with continuous stirring. The colloidal ferric oxyhydroxide formed is washed several times with water (5×75 mL) to remove chloride salt (also check with silver nitrate solution). Then ferric oxyhydroxide is suspended in 250 mL of water and added 1.8 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 11

Preparation of Sodium Ferric Gluconate Complex

To a solution of ferric chloride hexahydrate (6.3 g) in water (100 mL) is added gradually in about 10 minutes, ammonium hydrogencarbonate solution (5.5 g in 150 mL water) with continuous stirring. The colloidal ferric oxyhydroxide formed is washed several times with water (5×100 mL) to remove chloride salt (also check with silver nitrate solution). Then ferric oxyhydroxide is suspended in 250 mL of water and added 1.8 g of sodium gluconate (solid) at about 25° C. with continuous stirring for about 5 minutes. Then the reaction mixture is heated to about 70–80° C. for about 2 hours or until a dark brown color is formed. The ratio of ferric oxyhydroxide to sodium gluconate in this reaction is 2:1. The material passes infrared spectroscopic analysis.

EXAMPLE 12 (Comparative Example)

This example is with a hydroxide type of base.

To a solution of ferric chloride hexahydrate (8.3 g) in water (100 mL) is added gradually in about 10 minutes, 15 mL of ammonium hydroxide solution, 29.2%, 14.8 N (15 mL to 75 mL volume with DI water) with continuous stirring. The pH of the solution is neutral. The colloidal ferric hydroxide formed is washed several times with water (5×150 mL) to remove chloride salt (also check with silver nitrate solution). Then ferric hydroxide is suspended in 250 mL of water and added 2.1 g of sodium gluconate (solid) at about 25° C. with continuous stirring for about 5 minutes. Then the reaction mixture is heated to about 70–80° C. for about 3 hours. The ratio of ferric hydroxide to sodium gluconate in this reaction is 2:1. Reaction did not turn into dark brown color, and suspended solids are visible, indicating that the reaction is not successful.

EXAMPLE 13 (Comparative Example)

This example is with a hydroxide type of base.

To a solution of ferric chloride hexahydrate (6.7 g) in water (100 mL) is added gradually in about 10 minutes, sodium hydroxide solution (2.9 g in 50 mL water) with continuous stirring. The colloidal ferric hydroxide formed is washed several times with water (5×100 mL) to remove chloride salt (also check with silver nitrate solution). Then ferric hydroxide is suspended in 250 mL of water and added 2.7 g of sodium gluconate (solid) at about 25° C. with continuous stirring for about 5 minutes. Then the reaction mixture is heated to about 70–80° C. for about 4 hours. Reaction did not turn into dark brown color, and suspended solids are visible, indicating that the reaction is not successful. The ratio of ferric hydroxide to sodium gluconate in this reaction is 2:1.

What is claimed is:

1. The process for the preparation of sodium ferric gluconate complex in sucrose, comprising the steps of:

a) combining ferric chloride salt solution with alkaline earth metal and ammonium salts chosen from the group consisting of sodium carbonate, sodium bicarbonate, lithium carbonate, potassium carbonate, potassium bicarbonate, ammonium carbonate, ammonium bicarbonate and mixtures there of; to form the ferric oxyhydroxide;

b) combining ferric oxyhydroxide and sodium gluconate in solution to yield the sodium ferric gluconate complex; and c) combining sodium ferric gluconate with sucrose in solution to yield the desired sodium ferric gluconate complex in sucrose.

2. The process of claim 1 in which the ferric chloride salt is ferric chloride hexahydrate.

3. The process of claim 1 in which the alkaline earth metal salt is sodium carbonate.

* * * * *